(12) United States Patent
Sorace et al.

(10) Patent No.: US 6,606,622 B1
(45) Date of Patent: Aug. 12, 2003

(54) SOFTWARE METHOD FOR THE CONVERSION, STORAGE AND QUERYING OF THE DATA OF CELLULAR BIOLOGICAL ASSAYS ON THE BASIS OF EXPERIMENTAL DESIGN

(76) Inventors: James M. Sorace, 8620 Valleyfield Rd., Lutherville, MD (US) 21093; Gerald Canfield, 415 Gun Rd., Baltimore, MD (US) 21227

( * ) Notice: Subject to any disclaimer, the term of this patent is extended or adjusted under 35 U.S.C. 154(b) by 0 days.

(21) Appl. No.: 09/351,853

(22) Filed: Jul. 12, 1999

Related U.S. Application Data
(60) Provisional application No. 60/092,605, filed on Jul. 13, 1998.

(51) Int. Cl.[7] .............................................. G06F 17/30
(52) U.S. Cl. .......................................................... 707/4
(58) Field of Search ............................ 436/6; 707/3, 4, 707/10, 104.1, 503–508

(56) References Cited

U.S. PATENT DOCUMENTS

| | | | | |
|---|---|---|---|---|
| 5,619,708 A | * | 4/1997 | Ho ............................. | 358/453 |
| 5,737,592 A | * | 4/1998 | Nguyen et al. ............... | 707/10 |
| 5,804,436 A | | 9/1998 | Okun et al. | |
| 5,966,712 A | * | 10/1999 | Sabatini et al. ................ | 435/6 |
| 6,308,170 B1 | * | 10/2001 | Balaban ......................... | 435/6 |

FOREIGN PATENT DOCUMENTS

| | | | | |
|---|---|---|---|---|
| WO | WO 9623078 A1 | * | 8/1996 | ............ C12Q/1/68 |

OTHER PUBLICATIONS

National Center for Biotechnology Information http://www.ncbi.nlm.nih.gov.

\* cited by examiner

*Primary Examiner*—Jack M Choules
(74) *Attorney, Agent, or Firm*—Law Offices of Royal W. Craig

(57) ABSTRACT

An improved system for the conversion, storage and querying of cellular biological assay data on the basis of experimental design. The system relies on a library of data entry forms inclusive of separate forms for prompting a user to enter data characterizing the effects of a test agent applied to a test cell population's experimental group as compared to its control group with all other agents being identical between the experimental group and control group, and assay forms for prompting a user to enter data characterizing an experimental effect of an agent on said test cell population. The collected data is stored in different data storage records inclusive of a first data storage record incorporating characteristics of all agents entered by said agent data entry forms, and a second data storage record incorporating all experimental effects of agents as entered by said assay data entry forms. The first data storage record is related to the second data storage record by one or more shared fields. In addition, a library of query forms is maintained for allowing a user to submit queries about the experimental effect of any agent on the test cell population. The system includes suitable implementing hardware such as a conventional computer workstation with standard internal components. The system provide the ability to store and query heterogeneous data using a single data model in order to minimize difficulties associated in searching multiple databases. It supports a broad range of data including protein or mRNA expressions, as well as functional cellular data such as apoptosis or adherence.

2 Claims, 25 Drawing Sheets

FIG. 1: experimental notation for cellular response database

ENTRY FORM
CELL LIBRARY FORM
200

Species (Req.): Human — 22
Strain: — 24
Cell Name (Req.): Adherent Peripheral Blood Mononuclear Cells — 25
Cell Type (Req.): Macrophage — 26
Monoclonal: — 27
Primary Culture or Line: Line — 28
Commercial Supplier: — 29
Catalog Number: — 30
Organ of Origin: Blood — 31
ATCC Number: — 32
Note: — 33

Submit — 34

AgentEntry - Microsoft Internet Explorer

File Edit View Favorites Tools Help

Back Foreward Stop Refresh Home Search Favorites History Channels Fullscreen Mail Print Address

ENTRY FORM
REFERENCE FORM

400

First Author (Req.)  [Sorace JM]  — 61

Journal (Req.)  [Journal Name]  — 62

Title (Req.)  [Expression of Tissue Factor in Macrophages]  — 63

Volume (Req.)  [23]  — 64

Number (Req.)  [2]  — 65

First Page (Req.)  [535]  — 66

Date (Req.)  [4/1/98]  — 67

[Submit]  — 68

Fig. 6

ENTRY FORM
MEASUREMENT METHODS LIBRARY FORM        500

| | |
|---|---|
| Name | Tissue factor Elisa  — 70 |
| Classification | Protein Level — 71 |
| Response Units | PG/10,000 cells — 72 |
| Detects | Protein — 73 |
| Supplier | America Diagnostica — 74 |
| Catalog Number | 845 — 75 |

Submit — 76

| Table: | Field Name | Data Type | Description |
|---|---|---|---|
| Key Field | Agent | | |
| Yes | Agent_counter | AutoNumber | Key Field - Counts new agents |
| | Name | Text | Name of Agent e.g. IL-1 etc. |
| | Type | Text | Cytokine, chemokine, hormone, drug, Monoclonal Antibody, Virus, Knockout Gene, Transfected Gene, Antisense etc. |
| | Species | Text | Human, Mouse |
| | Supplier | Text | Company from which it was purchased. |
| | Sequence | Text | Sequence of peptide and oligonucleotide agents. |
| | AgentNote | Text | Annotation |
| | GeneProteinTarget | Number | Foreign Key from Gene-Protein_Library table, (example: anti-sense to what gene). |

*Fig. 12*

| Table: | Measurment_Method | | |
|---|---|---|---|
| Key Field | Field Name | Data Type | Description |
| Yes | Measurment_Method | AutoNumber | Key Field - number assigned to each new method |
| | Name | Text | Name of Assay. |
| | Response_Units | Text | How are the results quantitated (e.g. Counts per Minuet, Units per ML.). |
| | Classification | Text | mRNA, Protein Level, Protein activity, Cellular Function |
| | Detects | Text | If cellular function enter here (e.g. s-phase, apoptosis). |
| | Manufacturer | Text | Who supplies it. |
| | Catalog_Number | Text | What number to use to purchase |
| | Method_supplier_link | Text | Web site for supplier |
| | Method_Note | Text | Additional annotation. |

*Fig. 13*

Table: Gene_Protein_Library

| Key Field | Field Name | Data Type | Description |
|---|---|---|---|
| Yes | Gene_Protein_Counter | AutoNumber | Key field- number assigned to each new method |
|  | Gene_Name | Text | Name of gene |
|  | Species | Text | Human, Mouse etc. |
|  | GeneBank_ID | Text | Accession number for the gene's sequence |
|  | Memo | Text | Annotation |
|  | Sequence_Library | Text | If ID field above is other than GenBank |

*Fig. 14*

| Table: | Test_Cell_Population | | |
|---|---|---|---|
| Key Field | Field Name | Data Type | Description |
| Yes | Cell_Counter | AutoNumber | Key field- number assigned to each new cell population |
| | Species | Text | Human, Mouse etc. |
| | Strain | Text | What strain of mouse or other animal was the cell population derived From. |
| | Cell_Name | Text | Name of Cell (e.g. RAW 264.7) |
| | Cell_Type | Text | Macrophage, Neuron, T-Cell, Fibroblast |
| | Monoclonal | Yes/No | Select yes if cells are monoclonal. |
| | Primary_Culture_or_Line | Text | Choice of either primary culture or cell line |
| | ATCCNum | Text | ATCC Number |
| | Source | Text | Supplier. |
| | Organ_of_Orgin | Text | What organ were the cells harvested from (e.g. peripheral blood, spleen etc.). |
| | Note | Text | Annotation |
| | Catalog_Number | Text | Catalog number from supplier. |

*Fig. 15*

Table: Reference

| Key Field | Field Name | Data Type | Description |
|---|---|---|---|
| Yes | Reference_Number | AutoNumber | Key field- number assigned to each new reference. |
| | Author | Text | The last name and initials of the first author. |
| | Journal | Text | Journal or project name. |
| | Title | Text | Name of article or report |
| | Vol | Text | Volume of Journal |
| | Number | Text | Issue number of article. |
| | Page | Text | First page number of article. |
| | Date | Text | Date of article |
| | Submission_ID | Text | PubMed number of the article. |

*Fig. 16*

| Table: | Field Name | Data Type | Description |
|---|---|---|---|
| Key Field | Assay | | |
| Yes | Assay_Counter | AutoNumber | Key field- number assigned to each new Assay. |
| | Date | Date/Time | Date of Assay entry |
| | Test_Agent | Number | Foreign Key Agent Table Links the identity of the test agent to the assay table, must not be blank |
| | Control_Agent | Number | Foreign Key Agent Table Links the identity of the control agent to the Agents table, may have agent NULL if no control agent is used. |
| | Agent_Dosage_Units | Text | How is the test agent measured, often a concentration such as milligrams per milliliter. |
| | Pattern_of_Change | Number | Foreign key from Response Description Table, links to a qualitative summary of response such as up-regulated, down-regulated etc. |
| | Reference | Number | Foreign Key Reference Table, links to the source of the submission. |
| | Cell_Population | Number | Foreign Key Test_Cell_Population Table, links to the cells used in the assay. |
| | Target_Gene_Protein | Number | Foreign Key Gene_Protein_Library relates the assay to a target gene/protein if its activity or expression is measured |
| | Measurement_Method | Number | Foreign Key Measurement_Method Table |
| | DataSetType | Number | 1 is single point, 2 is dose response, 3 is kinetic |
| | Removal_Time_Offset | Number | Hours from removal of test agent to end of assay |
| | Assay_Note | Memo | Annotation |

*Fig. 17*

Table: Additional Agents in Assay

| Key Field | Field Name | Data Type | Description |
|---|---|---|---|
| Yes | Agent_Counter | Number | First component of a Compound Key Field is the Foreign Key from the Agent Table |
| Yes | Assay_Counter | Number | Second component of a Compound Key Field is the Foreign Key from the Assay Table |
| | Concentration | Number | The numerical value of the concentration of the additional agent. |
| | Concentration_Unit | Text | The units the above number corresponds to.. |
| | Addition_time_offset | Number | If the agent is added after the beginning of the assay enter the time in hours |
| | Removal_Time_offset | Number | If the agent is removed after the beginning of the assay enter the time in hours |
| | Notes | Text | Annotation |

*Fig. 18*

| Table: | Assay_Data | | |
|---|---|---|---|
| Key Field | Field Name | Data Type | Description |
| Yes | Assay_Counter | Number | First field of a compound key, Foreign Key from Assay table |
| Yes | Assay_Concentration | Number | Numerical value of concentration of Test Agent |
| Yes | Assay_Length | Number | Length in hours |
| | From | Number | Value measured in the control population of cells. |
| | From_Standard_Deviation | Number | Standard deviation of above. |
| | To | Number | Value measured in the experimental population of cells. |
| | To_Standard_Deviation | Number | Standard deviation of above. |

*Fig. 19*

| Table: Measurement_Ontology | | |
|---|---|---|
| Key Field | Field Name | Data Type | Description |
| Yes | Measurement_Counter | Number | First component of a compound key field is the foreign key from the Methods table. |
| Yes | Method_Ontology_value | Text | Second component of a compound key field is the value of the code (e.g. C0080129) |
| Yes | Method_Ontology_term | Text | Third component of a compound key field is the term (e.g. s-phase) |
|  | Method_Ontology_name | Text | Name of the ontology (UMLS in this example) |
|  | Method_Ontology_link | Text | URL for the ontology web site |

*Fig. 20*

Table: Response_Description

| Key Field | Field Name | Data Type | Description |
|---|---|---|---|
| Yes | Response_Type | AutoNumber | Key field- number assigned to each new response description |
| | Response_Description | Text | A brief description of the measured effect the test agent had on The Test Cell Population. For example up-regulated, down-regulated. |

Fig. 21

Pattern(s) of Response and Manuscript References for a Test Agent.

BACK TO GRD Homepage

| ASSAY # | TEST AGENT NAME | CELL NAME | SPECIES | GENE PROTEIN | CLASSIFICATION | DETECTS | PATTERN OF RESPONSE | FIRST AUTHOR | JOURNAL | VOL | PAGE |
|---|---|---|---|---|---|---|---|---|---|---|---|
| 1 | Thalidomide | U1 | Human | HIV-1 Reverse Transcriptase | Protein Activity | DNA Synthesis | Down regulated but still detectable | Makonkawkeyoon | PNAS | 90 | 5974 |
| 2 | Thalidomide | U1 | Human | HIV-1 Reverse Transcriptase | Protein Activity | DNA Synthesis | Down regulated but still detectable | Makonkawkeyoon | PNAS | 90 | 5974 |
| 3 | Thalidomide | U1 | Human | HIV-1 Reverse Transcriptase | Protein Activity | DNA Synthesis | Down regulated but still detectable | Makonkawkeyoon | PNAS | 90 | 5974 |
| 4 | Thalidomide | U1 | Human | HIV-1 Reverse Transcriptase | Protein Activity | DNA Synthesis | variable depending on conditions | Makonkawkeyoon | PNAS | 90 | 5974 |
| 5 | Thalidomide | U1 | Human | TNF-Alpha | Protein Activity | TNF-Alpha | Down regulated but still detectable | Makonkawkeyoon | PNAS | 90 | 5974 |
| 6 | Thalidomide | Fetal Microglia | Human | TNF-Alpha | Protein Activity | TNF-Alpha | Up regulated - present before stimulation | Phillip K. Peterson | Journal of Infectious Disease | 172 | 1137 |
| 33 | Thalidomide | ACH-2 | Human | TNF-Alpha | mRNA | RNA | Down regulated but still detectable | Makonkawkeyoon | PNAS | 90 | 5974 |

Detailed data by Assay #: [ ]

SEARCH

Description: This query presents the name of the test agent as well as the name and species of the cells used in the assay. It links this information with the name of the gene-protein being measured (if any), the classification of the assay (e.g. was a protein level or cell function such as apoptosis measured), what the assay detects and what the general pattern of response was (e.g. was the mRNA level or cell function increased or decreased). The final four columns present the reference information. Additional information can be obtained by using the "Detailed data by Assay #" query to drill down on an assay of interest.

FIG. 22

| TEST AGENT | ASSAY # | ADDITIONAL AGENT(S) |
|---|---|---|
| Thalidomide | 1 | HIV-1 |
| Thalidomide | 1 | Phorbol 12-myristate 13-acetate |
| Thalidomide | 2 | LPS |
| Thalidomide | 2 | GM-CSF |
| Thalidomide | 2 | HIV-1 |
| Thalidomide | 3 | GM-CSF |
| Thalidomide | 3 | HIV-1 |
| Thalidomide | 4 | IL-6 |
| Thalidomide | 4 | LPS |
| Thalidomide | 4 | HIV-1 |
| Thalidomide | 5 | IL-6 |
| Thalidomide | 5 | HIV-1 |
| Thalidomide | 5 | IL-3 |
| Thalidomide | 6 | LPS |
| Thalidomide | 33 | HIV-1 |
| Thalidomide | 33 | Phorbol 12-myristate 13-acetate |

Detailed data by Assay #: 

Search

Description: This query presents the name of the test agent and the assay in which it was used. It links this information with the name of the additional agent(S) used in the experiment. Note that assays with more than one additional agent are listed on consecutive rows. Additional information can be obtained by using the "Detailed data by Assay #" query to drill down on an assay of interest.

FIG. 23

| Assay Num. | Test Agent Name | Agent Type | Agent Note | Gene/Protein Name | SPECIES | Gene Note | GenBank Num |
|---|---|---|---|---|---|---|---|
| 158 | pCMV6-KD-Akt-HA | TRANSFECTED GENE | Kinase-defective (codon 179 K to M) | AKT | MURINE | Serine-Threonine Kinase | S53364 |
| 157 | pCMV6-Myr-Akt-HA | TRANSFECTED GENE | Activated AKT insert (SRC myrisoylation) | AKT | MURINE | Serine-Threonine Kinase | S53364 |
| 156 | pCMV6-Akt-HA | TRANSFECTED GENE | Wild type AKT insert | AKT | MURINE | Serine-Threonine Kinase | S53364 |
| 155 | pcDNA3-AU1-BAD | TRANSFECTED GENE | AU1 epitope taged BAD | BAD | MURINE | Distant member BCL_2 family | Q61337 |
| 192 | anti-CD28 | MONOCLONAL ANTIBODY | | CD28 | HUMAN | | Hs.1987 |
| 191 | anti-CD28 | MONOCLONAL ANTIBODY | | CD28 | HUMAN | | Hs.1987 |
| 176 | Anti-IL-12 mAb | MONOCLONAL ANTIBODY | | IL-12 | HUMAN | | |
| 153 | Wortmannin | DRUG | PI 3-Kinase Inhibitor | PI 3-kinase | MURINE | | Mm.3810 |
| 151 | Wortmannin | DRUG | PI 3-Kinase Inhibitor | PI 3-kinase | MURINE | | Mm.3810 |

Detailed data by Assay #:

Search

Description: This query presents the name of the test agent and the assay in which it was used. In addition, it gives the classification of the test agent (e.g. drug, cytokine, monoclonal antibody,transfected gene etc) as well as any relevant information in the note field. The gene/protein which the test agent is related to is described in the following 4 fields. Thus information concerning the enzyme inhibited by a drug, the antigen of a monoclonal antibody or the gene expressed in a transfected plasmid will be found here. This includes the name of the gene/protein, the species, a brief note field, and its GenBank number. Additional information can be obtained by using the "Detailed data by Assay #" query to drill down on an assay of interest.

FIG. 24

Pattern(s) of Response and Manuscript References for a UMLS code by Cell.

Back to CRD Homepa

| Term | Value | ASSAY # | TEST AGENT NAME | CELL NAME | SPECIES | GENE PROTEIN | CLASSIFICATION | DETECTS | PATTERN OF RESPONSE | FIRST AUTHOR | JOURNAL | VOL | PAGE |
|---|---|---|---|---|---|---|---|---|---|---|---|---|---|
| Vascular Smooth Muscle | C0026844 | 136 | TGF-Beta1 | Vascular Smooth Muscle Atherosclerosis | Human | Null | Cellular Function | DNA Synthesis | Basal level of expression unchanged | McCaffrey TA | J. Clin. Invest. | 96 | 2667 |
| Vascular Smooth Muscle | C0026844 | 169 | TGF-Beta1 | Vascular Smooth Muscle Normal | Human | Null | Cellular Function | DNA Synthesis | Down regulated but still detectable | McCaffrey TA | J. Clin. Invest. | 96 | 2667 |

Detailed data by Assay #: [ ]

Search

Description: This query presents the name of the test agent as well as the name and species of the cells used in the assay. It links this information with the name of the gene-protein being measured (if any), the classification of the assay (e.g. was a protein level or cell function such as apoptosis measured), what the assay detects and what the general pattern of response was (e.g. was the mRNA level or cell function increased or decreased). The final four columns present the reference information. Additional information can be obtained by using the "Detailed data by Assay #" query to drill down on an assay of interest.

FIG. 25

SOFTWARE METHOD FOR THE CONVERSION, STORAGE AND QUERYING OF THE DATA OF CELLULAR BIOLOGICAL ASSAYS ON THE BASIS OF EXPERIMENTAL DESIGN

CROSS-REFERENCE TO RELATED APPLICATIONS

The present application is based on U.S. provisional application serial No. 60/092,605 filed on Jul. 13, 1998 by Sorace et al. for their "A SOFTWARE METHOD FOR THE CONVERSION, STORAGE AND QUERYING OF THE DATA OF CELLULAR BIOLOGICAL ASSAYS ON THE BASIS OF EXPERIMENTAL DESIGN".

BACKGROUND OF THE INVENTION

1. Field of the Invention

The present invention relates to a bioinformatics approach and, more particularly, to a software method for the conversion, storage and querying of the data of cellular biological assays on the basis of experimental design that allows storage and retrieval of data concerning changes in in-vitro cellular functions associated with stimuli such as cytokines, hormones, chemochimes, transfected genes, infectious agents, and drugs.

2. Description of the Background

To date, paper publications are the principle form in which scientific information is exchanged. However, there is a significant opportunity in the field of bioinformatics in determining how to store and retrieve information electronically so that future discoveries can be made. Key-word search engines like Pubmed® allow users to find articles based on Boolean combinations of MESH headings, author, or keyword string searches. More recently, interfaces such as ENTREZ® allow users to cross-reference manuscripts with GenBank sequence entries. Still, current functional bioinformatics approaches are handicapped by the inability to store functional data at all, or by a scattering of data across heterogeneous databases that are difficult to link and query. Specifically, the above-described and other known approaches do not support queries linking a test cell population's expression of proteins and other traits, to the experimental conditions in which they were measured. For example, key word searches do not enable a user to clearly specify the context in which a cytokine is used. Thus, the query "INF-Gamma up regulated" may retrieve the genes which INF-gamma up regulates, or it may retrieve conditions in which INF-gamma is itself increases. Consequently, as biology moves into the post-genome era there is a need to develop better systems for the storage, retrieval and interpretation of biological information.

U.S. Pat. No. 5,804,436 to Okun et al. shows an Apparatus and Method for Real-time Measurement of Cellular Response in which a homogeneous suspension of living cells is combined with a concentration of a test compound. The cellular response of the living cells is measured in real time as the cells in the test mixture are flowing through a detection zone. The apparatus may be used in automated screening of libraries of compounds, and is capable of real-time variation of concentrations of test and standard compounds and generation of dose/response profiles. This implies some data entry, storage and retrieval. However, the mechanics for the storage, retrieval and interpretation of biological information are not taught or suggested, and it is not clear whether or how a test cell population's expression of MRNAs proteins and other traits can be linked to the experimental conditions in which they were measured.

It would be greatly advantageous to provide a method for the data entry, storage and retrieval that supports queries linking a test cell population's expression of genes proteins and other traits, to the experimental conditions in which they were measured, as well as to provide a framework for other, more complex information operations.

SUMMARY OF THE INVENTION

Accordingly, it is an object of the present invention to provide a software method for the conversion, storage and querying of cellular biological assay data on the basis of experimental design, inclusive of queries concerning changes in in-vitro cellular functions associated with stimuli such as cytokines, hormones, chemochimes and drugs, transfected genes, infectious agents, or physical perturbations such as temperature or ionizing radiation.

It is another object to support a broad range of data including protein or mRNA expressions, as well as functional cellular data such as apoptosis or adherence.

It is still another object to provide the ability to store heterogeneous data using a single data model in order to minimize difficulties associated in searching multiple databases.

It is still another object to provide for the storage of heterogeneous cell lines.

It is a further object to to allow the measurements, cells and conditions to be coded by user-determined ontologies.

According to the present invention, these and other objects are accomplished by providing a system for the conversion, storage and querying of the data of cellular biological assays on the basis of experimental design. The method employed by the system includes the maintenance of a library of data entry forms inclusive of materials and method forms for prompting a user to enter data characterizing all agents (e.g., culture conditions) applied to a test cell population (inclusive of both an experimental group and a control group), experimental design forms for prompting a user to enter data characterizing the experimental design (inclusive of all test agents, control agents and additional agents), and experimental results forms for prompting the user to enter data characterizing an experimental effect of a specific agent on an experimental group as compared to the control group of a test cell population.

Preferably, the materials and methods data entry forms include an agent library form, a test cell library form, a gene/protein library form, a references library form, and a measurement methods library form. The information gained through the above forms is filtered into and combined with further information collected via the experimental design library which includes a general experimental design form, and an additional agents form. Finally, the experimental results library includes an experimental data form that allows a comprehensive description of the experimental results.

The collected data is stored in respective data storage records inclusive of a first data storage record incorporating characteristics of the materials and methods as entered via the corresponding library of forms (Agent, Test Cells, Target Genes, References (if specified), and Measurement Method). The data also includes a second data storage record incorporating characteristics of the experimental design as entered via the corresponding library of forms (inclusive of all test agents, control agents and additional agents). In addition, a third data storage record is accumulated and this defines the experimental results that quantify the effect of a specific agent on an experimental group as compared to the control group of a test cell population.

The three data storage records are inter-related by one or more shared fields.

In addition to the data entry forms, a library of query forms is maintained for allowing a user to submit queries about the experimental effect of any agent on the test cell population. Separate query forms may be maintained for allowing a user to enter queries related to a cellular biological assay, for allowing a user to enter queries related to genes that said assays are related to, and for allowing a user to enter queries related to combinations of agents used in said assay.

The above-described software method is combined with suitable hardware for implementation of the entire system. The hardware may include a conventional computer workstation with standard internal components such as a microprocessor with peripheral chipset mounted on an appropriate motherboard, storage, a monitor, a modem, a standard input device such as a mouse, and an operating system such as Microsoft Windows. All forms and data libraries may be authored using conventional relational database software such as Microsoft Access®.

BRIEF DESCRIPTION OF THE DRAWINGS

FIG. 4 is an example of a test cell library data entry form 200.

FIG. 5 is an example of a Gene/Protein library data entry form 300.

FIG. 6 is an example of a reference library data entry form 400.

FIG. 7 is an example of an Measurement Method Library data entry form 500.

FIG. 8 is an example of the "Add New Assay: Experimental Design Form" 700.

FIGS. 12–21 are examples of suitable table structures for the above-described tables as follows: Agent (FIG. 12), Measurement Method (FIG. 13), Gene/Protein (FIG. 14), Test Cell Population (FIG. 15), Reference (FIG. 16), Assay (FIG. 17), Additional Agents (FIG. 18), and the Assay Data Table (FIG. 19), Measurement_Ontology (FIG. 20), and Response Description (FIG. 21).

FIG. 22 shows information for the test agent thalidomide (a Drug).

FIG. 23 shows all the additional agents thalidomide has been assayed with.

FIG. 24 shows the relationships between a group of agents and their target genes.

FIG. 25 shows data from a query for cell lines coded for "vascular smooth muscle".

DETAILED DESCRIPTION OF THE PREFERRED EMBODIMENTS

The data entry, storage and querying capabilities of the present system are based on a model involving three types of biological entities: the test cell population, the method for measuring a biological response that may include measuring the activity of a target gene or protein whose level and/or activity is assayed, and one or more agents that are tested to see if they alter the activity of a target gene or protein. Agents may include protein molecules such as cytokines, hormones, chemochimes, sterol hormones or drugs, transfected genes, infectious agents, or physical perturbations such as temperature or ionizing radiation. Often, their common property is that, at a specific time point in the experiment, the investigator adds them at a predetermined concentration. Various combinations of agents may be used within any experiment, and dose response and kinetic data may be presented. However, the model used herein allows comparisons between two groups of test cells that differ only by treatment with one agent (with all other agents in common between the two grous).

Figure 1:
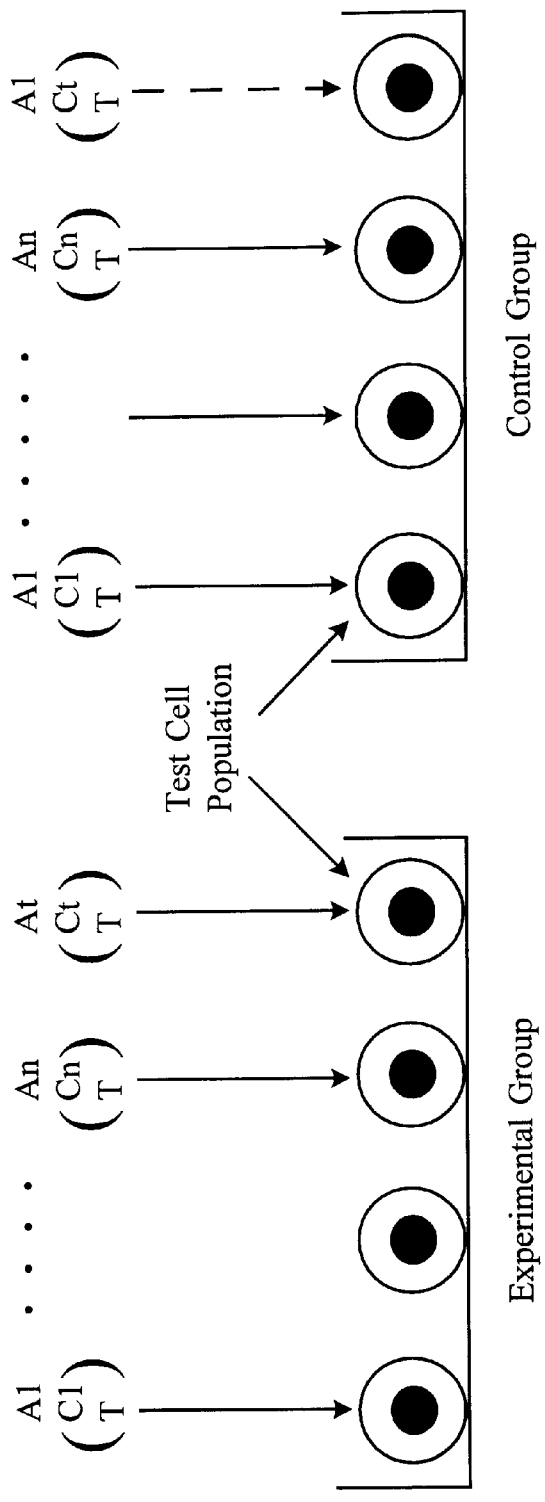
FIG. 1 illustrates the agent model by which one or more agents (i.e., culture conditions) A1 . . . An are applied to a test cell population including both an experimental group and a control group. The test agent At is applied only to the experimental group of cells, while the control agent Ac may be applied only to the control group of cells.

FIG. 1 illustrates the agent model by which one or more agents A1 . . . An are applied to a test cell population including both an experimental group and a control group. For ease of description, the term agent shall be limited to soluble molecules (e.g. drugs, cytokines, chemochimes, hormones, or other biomolecules) that are added to the culture supernatant of a test cell population. For example, LPS is an agent that induces tissue factor (a procoagulant molecule) production in human macrophages. In this case, human macrophages are the test cell population, while the measurement of tissue factor is the response of interest. All experiments are required to have at least one test agent, and there may be many additional agents including a control agent. On the other hand, there may be more complicated experiments, e.g., a scientist testing a drug to determine if it inhibits the production of tissue factor by LPS. Here two agents would be used, the drug and LPS. LPS would be applied to both the experimental and control groups of human macrophages, while the drug would be applied only to the experimental group. The difference in tissue factor production between the two groups would then be determined. To model these more complex experimental designs, the present system recognizes three types of agents: 1) Test Agents: are added only to the experimental group of the assay (in the second example above, the experimental drug is the test agent); 2) Additional Agents: these are added under identical conditions to both the experimental and control group of cells (in the second example above, LPS is an additional agent); 3) Control Agents: this represents a group of agents that are added only to the control population. Representative examples include control olgonucleotides in anti-sense experiments, or control: monoclonal antibodies if the test agent is also a monoclonal antibody.

The results of the experiments are represented by assays. In the second example noted above, the researcher could adequately describe his experimental findings (including relevant controls) by the following three assays:

Assay 1: Contains the data regarding changes in tissue factor production in human macrophages with LPS as the test agent.

Assay 2: Contains the data regarding changes in tissue factor production in human macrophages with the experimental drug as the test agent (At as in FIG. 1).

Assay 3: Contains the data regarding changes in tissue factor production in human macrophages with the experimental drug as the test agent and LPS as an additional agent.

The system according to the present invention provides a means for efficient conversion, storage and querying of the data of cellular biological assays based on the above-described model of experimental design, whereby changes in in-vitro cellular functions associated with stimuli such as cytokines, hormones, chemochimes and drugs can be stored and queried in a meaningful way. The present system entails a specific data entry structure, a specific data storage structure, and a specific approach to querying the data.

Figure 2:
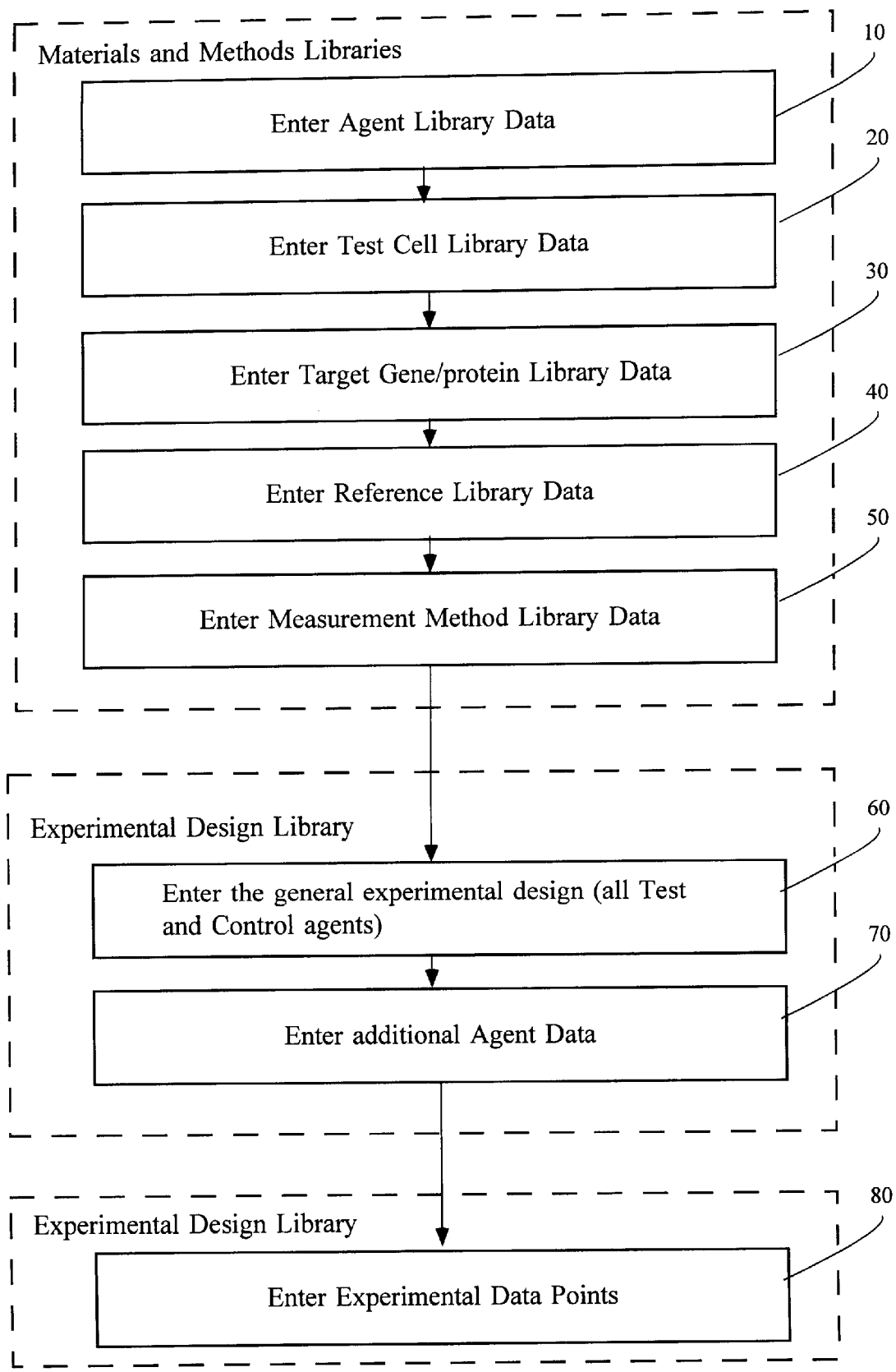
FIG. 2 is a functional flow chart showing the steps involved in the conversion, storage and querying of the data of cellular biological assays per the software method of the present invention.

FIG. 2 is a functional flow chart showing the steps involved in the conversion, storage and querying of the data of cellular biological assays per the software method of the present invention. At steps 10–80 data is entered pursuant to a particular format. The data storage format of the present system contains three types of tables, materials and methods library tables, experimental design library tables, and experimental results tables. The materials and methods library tables contain background data on all agents (e.g. cytokines, hormones, chemochimes and drugs), test cell populations, target proteins/genes, references (if specified), and the methods used to measure the test cell population's response. Data is entered into these tables at steps 10–50 using corresponding library forms, and once the appropriate information is added to the library tables it is always available for future use and need not be entered again. Specifically, the materials and methods library tables include: 1) an Agent table supported by entry of Agent data at step 10 via an Agent Library Form; 2) a Test Cells table supported by entry of Test Cells data at step 20 via a Test Cells Library Form; 3) a Gene/Protein table supported by entry of Gene/Protein data at step 30 via a Gene/Protein Library Form; 4) a Reference table supported by entry of Reference data at step 40 via a Reference Library Form; and 5) a Measurement Method table supported by entry of Measurement Method data at step 50 via a Measurement Method Library Form.

Figure 3:
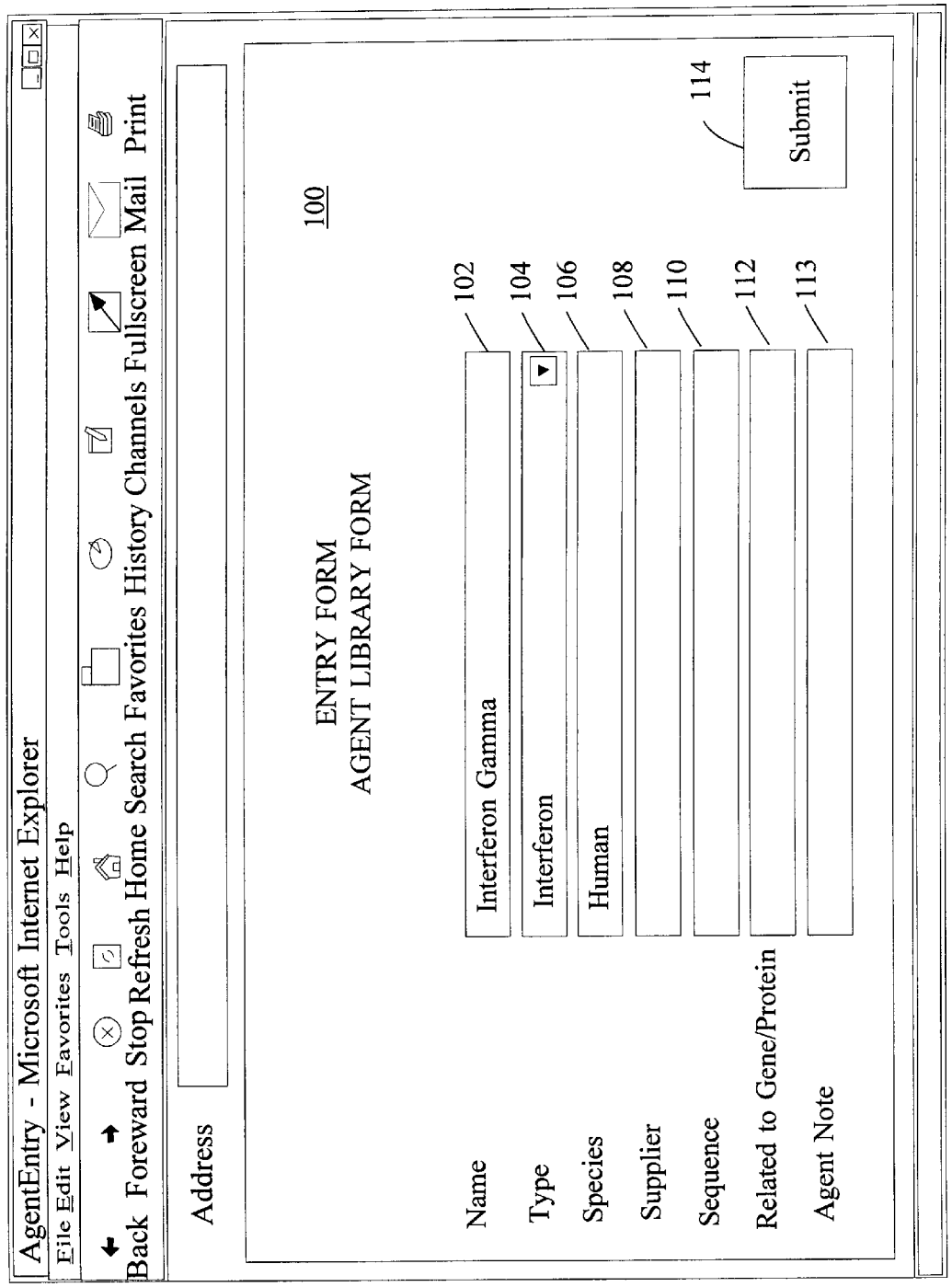
FIG. 3 is an example of an agent library data entry form 100 by which the characteristics of all potential agents can be entered.

FIG. 3 is an example of an agent library data entry form 100 by which the characteristics of all potential agents can be entered. The name of the agent is entered in box 102, and the appropriate type of the agent is selected in drop-down list 104. For example interferon gamma would be identified as such by NAME in box 102 and classified as type interferon in box 104. TNF-alpha would be type cytokine, thalidomide would be a drug. This method is very flexible and allows for physical (e.g. culture temperature) and genetic (e.g. transfected gene) types as well. Indeed any culture conditions can be treated this way. Additional information includes the agent's species at box 106, supplier at box 108, and sequence at box 110. The sequence typed into box 110 contains the actual amino acid nucleotide sequence of the test agents. In addition, any gene/protein to which the agent is related is typed into box 112. Thus in cases were the test agent is a transfected gene, information pointing to its gene bank number and other data can be stored and retrieved by the data in box 112. This feature is also useful in other agent types. For example agents of types "monoclonal antibody" can be related to the protein product to which it binds. Or agents of type "oligonucleotide" can be related to the mRNA gene product that they down regulate in antisense experiments. This allows subsequent retrieval of experimental data based on the gene products which are either used as agents directly (e.g. transfection or direct addition of the gene product) or indirectly (e.g. drugs, antibodies, anti-sense etc.). A discretionary free-text field Agent Note box 113 is provided for miscellaneous notes. To facilitate entering Agent library data, the data entry form 100 is replete with help and prompts for the type of data called for in data entry. When all data is entered and the researcher hits the submit button 114, the system first checks to determine if the information already exists. If an accurate match can be found, the corresponding library form need not be submitted.

Referring back to FIG. 2, at step 20 Test Cell Library data is entered, and FIG. 4 is an example of a test cell library data entry form 200.

The Species that the cells were derived from is entered into box 22. For example, Human.

The Strain of cells is entered at box 24. For example, if murine was the strain C57 black may be entered.

The Cell Name is entered at box 25. Examples include RAW 264.7, L-cells, peripheral blood mononuclear cells, peritoneal exudate cells, fetal microglial etc.

Example: Adherent Peripheral Blood Mononuclear Cells.

The Cell type is entered at box 26. Examples include macrophage, promonocyte, endothelial etc.

At check box 27, the researcher indicates whether the cell population is Monoclonal.

The Primary Culture is indicated at drop-down list 28. For example, if the cells have been immortalized for long term culture, the researcher selects "Line". On the other hand, if they are isolated for brief in-vitro passage the researcher selects "Primary Culture".

The Commercial Supplier is entered at box 29 if purchased or obtained from a supplier.

The Catalog Number is entered at box 30 if purchased or obtained from a tissue collection.

The Organ of Origin is entered at box 31 if it is a primary cell line. Examples include blood, spleen, liver, brain, coronary artery etc.

The ATCC Number is entered at box 32 if known, and other miscellaneous notes can be entered at box 33.

When all data is entered and the researcher hits the submit button 34, the system first checks to determine if the information already exists. If an accurate match can be found, the corresponding library form need not be submitted.

Figure 5:
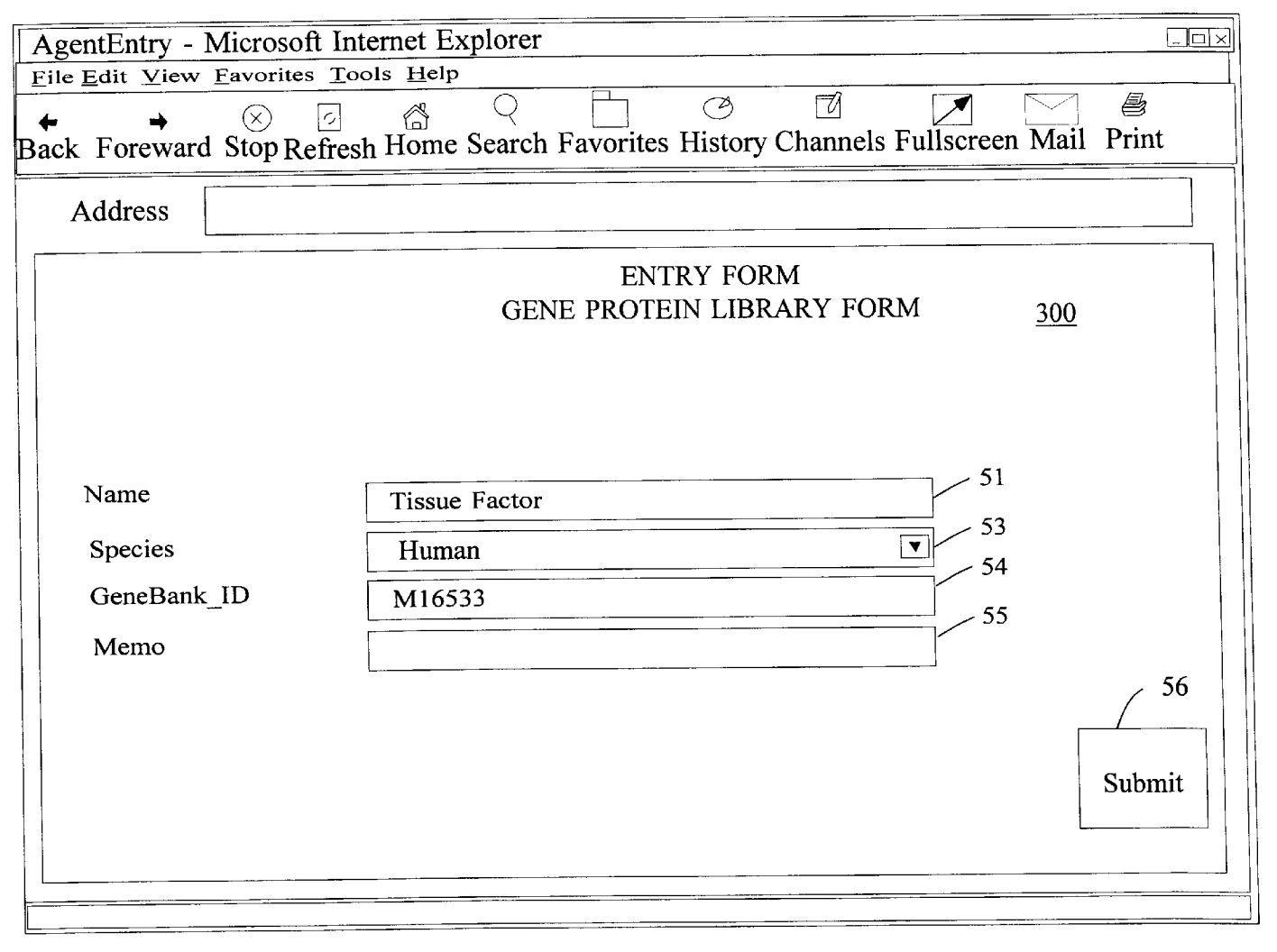

Referring back to FIG. 2, at step 30 the Gene/Protein data is entered, and FIG. 5 is an example of a Gene/Protein library data entry form 300.

The Gene/Protein Name being measured is entered in box 51. Examples include IL-2, tissue factor, HIV reverse transcriptase, Prostaglandin E-2 etc.

The Species in which the measurement is made is entered at drop-down list 53. Examples include human, mouse, etc.

The GenBank_ID, if applicable, is entered at box 54. This number corresponds to the sequence of the gene.

In the Memo box 55 any additional information as necessary can be entered. When all data is entered and the researcher hits the submit button 56, the system first checks to determine if the information already exists. If an accurate match can be found, the corresponding library form need not be submitted.

Referring back to FIG. 2, at step 40 Reference Library data is entered, and FIG. 6 is an example of a reference library data entry form 400.

At step 61 the Author is entered. Preferably, this is the first author of the article, last name first, followed with a space, and then with the initials.

At box 62, the Journal name is entered.

At box 63, the Title is entered. Example: Expression of Tissue Factor in Macraphages.

At box 64, the journal Volume number is entered.

At box 65, the number of the issue is entered.

At box 66, the article's first page number only is entered.

At box 67, the date of publication is entered.

Once again, when all data is entered and the researcher hits the submit button 68, the system first checks to determine if the information already exists. If an accurate match can be found, the corresponding library form need not be submitted.

Referring back to FIG. 2, at step 50 Measurement Method Library data is entered, and FIG. 7 is an example of an Measurement Method Library data entry form 500.

A brief descriptive Name for the assay is entered in box 70. Examples are L-929 cytotoxicity, Tissue Factor ELISA (a commercially available system name the vendor uses).

The Classification is entered at drop-down list 71. For instance, if the method detects mRNA the same is selected. If the level of a protein is measured (e.g., ELISA) select "Protein Level". If the method determines the activity of a specific protein select "Protein Activity". Finally, if a cellular function is measured (i.e. proliferation, apoptosis) select "Cellular Function".

At box 72 the researcher selects how the measure quantified. Examples include units/ml, micromolar, % cytotoxicity etc. In general enter the units that were used in the manuscript table or figure describing the experiment are entered here. If results are compared visually, enter "visual comparison".

At box 73, the following guidelines are used for data entry:

1) If the method detects the activity of a protein, enter a 2 to 3 word description. Examples include reverse transcriptase activity, prothombinase activity, and TNF activity.

2) If the assay detects a cellular trait or function, enter a one to three word description. Examples include adherence, apoptosis, cytotoxicity, growth inhibition, and cell-cycle analysis.

3) If the method detects mRNA or protein levels, a few additional words can be entered if necessary. Example: Protein At box 74 the Supplier is entered if a commercial system is used. Example: America Diagnostica.

At box 75 the Catalog Number is entered if a commercial system was used. Example: 845.

Once again, when all data is entered and the researcher hits the submit button 76, the system first checks to determine if the information already exists. If an accurate match can be found, the corresponding library form need not be submitted.

Once the materials and methods library tables are completed per steps 10–50 (using corresponding library forms), and the tables are filled with all background data on all agents (e.g. cytokines, hormones, chemochimes and drugs), test cell populations, target proteins/genes, references (if specified), and the methods used to measure the test cell population's response, then this data is always available for future use and need not be entered again. Consequently, entering a new assay becomes a very simple process.

In addition to the materials and methods tables, the data storage format of the present system contains experimental design library tables. Data is entered into these tables at steps 60–70 using a corresponding library of forms, and once the appropriate information is added to the library tables it is always available for future use and need not be entered again. Specifically, the experimental design library tables include: 1) The Assay library table (that contains general experimental design information) is filled via an "Add New Assay: Experimental Design Form"; and 2) The Additional Agents Table that is filled via an "Add New Assay: Non-Test/Control Agents Form".

Referring back to FIG. 2, at step 60 the General Experimental Design is entered. This requires specifying the test and control agents (if any) used in the experiment's design.

Figure 8:
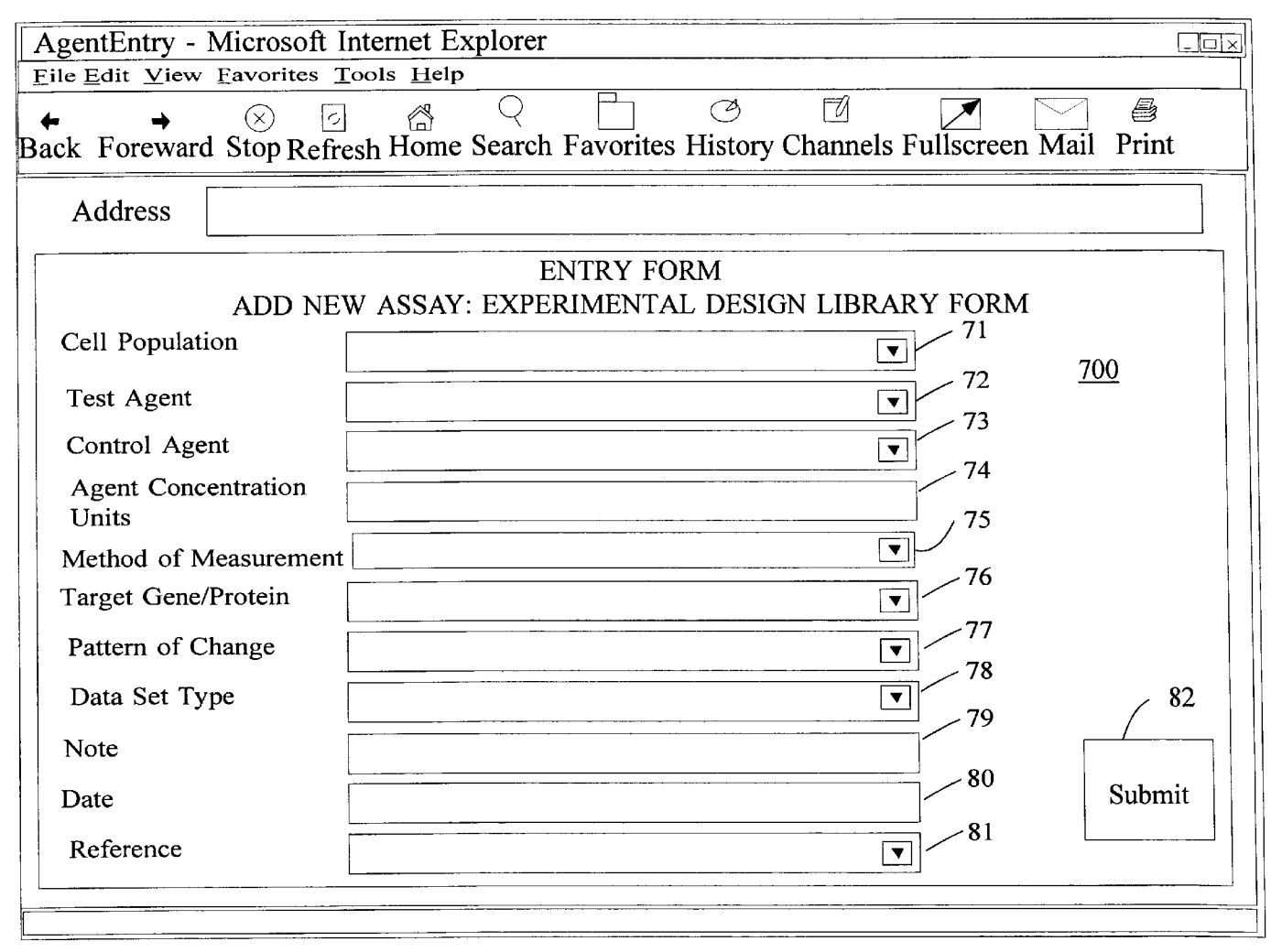

FIG. 8 is an example of the "Add New Assay: Experimental Design Form" 700. Data entered into the methods and materials tables become drop-down lists in form 700.

At drop-down list 71 the Cell Population is selected by choosing the appropriate cell population from the cell library (see above). Example: Adherent Peripheral Blood Mononuclear Cells, Macrophage, Human.

At drop-down list 72 the Test Agent is selected from the agent library. To do this, the researcher must determine which agent is unique (one to one) to the experimental group being entered and this will be entered as the TEST AGENT. Example: Anti-Tissue Factor-Antisense, oligonucleotide, NA, University Biopolymer Laboratory.

At drop-down list 73 the Control Agent is selected from the agent library. In many experimental designs no control agent is used, and in this case choose "null". On the other hand, if the researcher determines that the negative control group has a control agent unique to it this will be entered as the CONTROL AGENT. Example: Anti-Tissue-Factor Random, Oligonucleotide, NA, University Biopolymer laboratory.

At box 74 the Agent Concentration Units are entered. These are the concentration units used to measure the agents. Examples include Units/ml, micrograms per ml., micro molar etc. The actual numerical value will be an entered later. Example: micro-molar.

At drop-down list 75 the Method of Measurement is selected. This list includes the appropriate methods for detecting the gene/protein or cellular function that is being measured in the test cell population from the Methods library. Exemplary Field values are as follows: Classification, Name, Detects, Response Units, Supplier, Catalog number.

At drop-down list 76 the Gene/protein is selected. This list includes the appropriate Gene/protein from the Gene/protein library. If a general cellular property is measured select the "null" option. Exemplary Field Values include Name, Species, GenBank_ID. Example: Tissue Factor, Human; M16553.

At drop-down list 77 the Pattern of Change is selected from the list provided. Example: Down regulated but still detectable.

At box 78 the Data Set Type is entered. Examples include: Single point, dose response or kinetic.

At box 79 Assay Notes can be entered. If desired a short written note can be entered. Example: LPS added 9 hours after test agent.

At box 80 the assay Date is entered.

Finally, at drop-down list 81 the Reference is selected. This list includes the appropriate Reference from the Reference library.

Once again, when all data is entered and the researcher hits the submit button 82, the system first checks to determine if the information already exists. If an accurate match can be found, the form need not be submitted.

Figure 9:
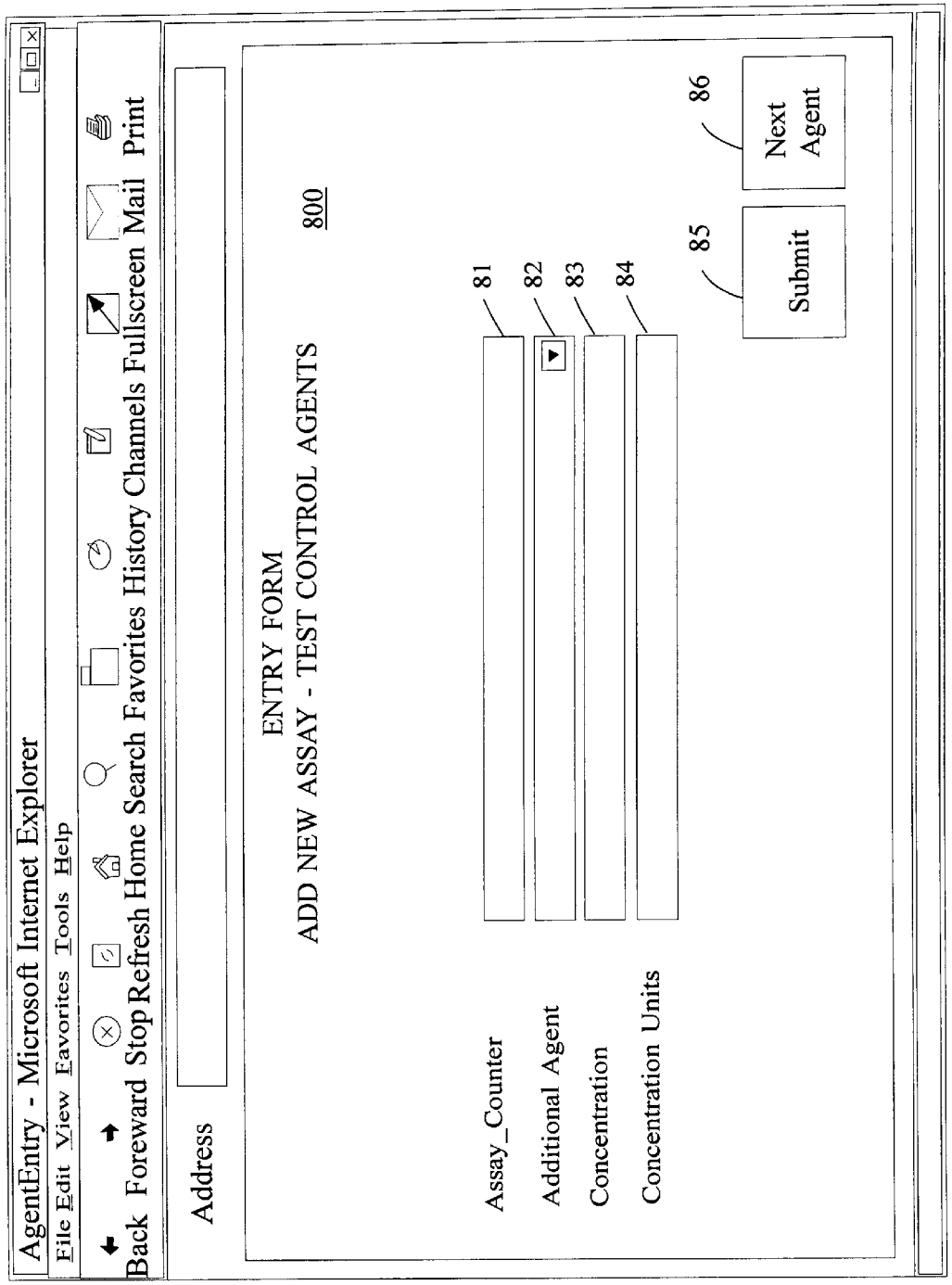
FIG. 9 is an example of the "Add New Assay: Non-Test/Control Agents Form" 800.

Referring back to FIG. 2, if the experiment uses Additional Agents, this information must be entered at step 70. The Additional Agents include all other agents (zero to many) found in both the experimental and control groups. FIG. 9 is an example of the "Add New Assay: Non-Test/Control Agents Form" 800.

An Assay Counter is assigned by the system and is displayed in box 81.

At drop-down list 82, the Additional Agent is selected from the agent library. Exemplary Field values are as follows: Name, Type, Species, Supplier. Example: LPS, Endotoxin, Sigma At drop-down list 83, the Concentration is entered. This is the numerical value for the agent's concentration. Example: 100.

At box 83 the Concentration Units are entered. This is the corresponding numerical value (Units/Ml, Micro-molar).

Finally, the researcher hits the Submit button 85 to enter the Non-Test/Control Agent data. The Next Agent button 86 clears the form data to begin entry of another.

Once the general experimental design library tables are completed per steps 60–70 (using corresponding library forms), and the tables are filled with all background data on the experimental design, then this data is available for future use and need not be entered again. Finally, entering specific test data becomes a very simple process.

In addition to the materials and methods tables and general experimental design library tables, the data storage format of the present system contains actual experimental data tables for each assay. Data is entered into these tables at step 80 using a corresponding library forms, and once the appropriate information is added to a corresponding library table.

Figure 10:
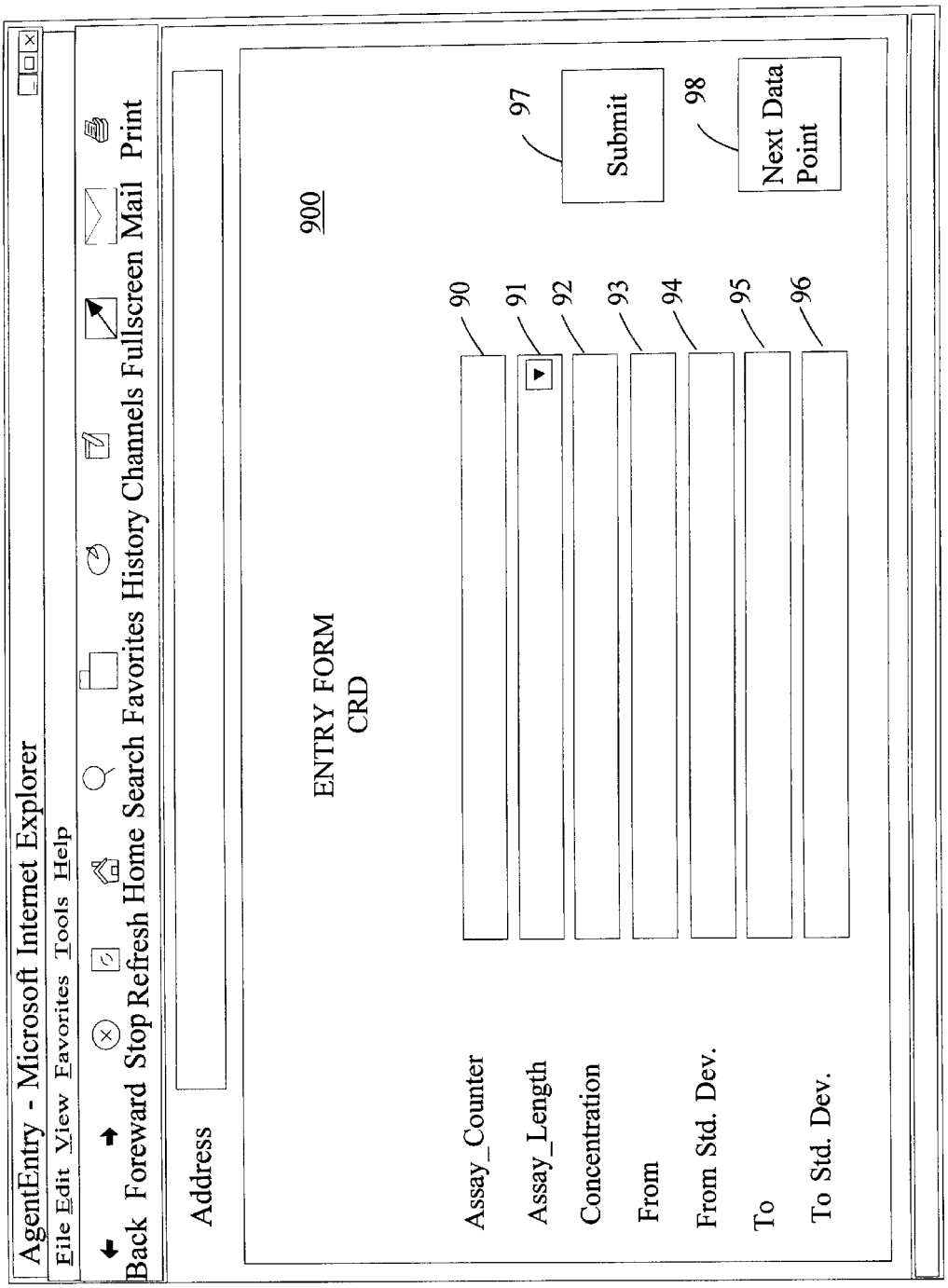
FIG. 10 is an exemplary "Add New Assay: Quantitative Data Form" 900.

Referring back to FIG. 2, at step 80 actual experimental data is entered such as the time points, test agent concentration and quantitative response values for each experimental point. FIG. 10 is an exemplary "Add New Assay: Quantitative Data Form" 900.

An Assay_Counter is self-assigned by the system and is displayed in box 90.

At box 91 the Assay Length is entered in hours, for dose response experiments this should be the same for data point while for kinetic experiments it should differ.

At box 92 the Test Agent Concentration is entered. This is the numerical value for the concentration. The units for this measurement, and its name, were previously entered in the test/control agent concentration field of the assay form (see above). For kinetic experiments the same value should be submitted each time while for dose response the test agents concentration should vary.

The next four boxes 93–96 allow entry of data that only applies if the method of measurement of the assay produces a quantitative result. The units of these measurements have already been entered in the Method of Measurement table. Specifically, at box 93 the From value is entered. This is a numerical value based on the control population. The units have already been entered in the methods table.

At box 94 the From Std. Dev. (from standard deviation of the above measurement) is entered.

At box 95 the To: indicates the numerical value of the experimental group.

At box 96 the To Std. Dev. Is completed to indicate the amount of one standard deviation for the above measurement.

The data is submitted by completing the form as needed and pressing button 97. The Next Data Point button 98 clears the form data to begin entry of another, and the process can be repeated for each data point. This completes assay data entry instructions.

A researcher that wishes to become familiar with specific results must deal with the information in the published article format. This is an efficient mechanism for learning the details of experimental results, but is not efficient for summarizing trends across experimental efforts. This sections gives an example of the data flows and programs needed to create data warehouses that allow researchers to issue focused queries about specific experimental results. Once the trends are established, the researcher may have to go back to the articles for important details. The example given here is conceptually useful for creating other data warehouse in similarly structured areas of experimental effort.

A researcher that has an article accepted for publication or is working on a project at a pharmaceutical company would be required to submit a subset of the results using a system such as described herein. This is a simple task that should not take more than 20 minutes of the researchers time. All forms are web-based and the databases are maintained at the repository site.

2. Data Storage Structure

The present system is also based on a specific data storage structure based on the above-described model that allows efficient querying of the data of cellular biological assays. Once all necessary library and assay data is entered it is stored in a relational format that allows agents to be queried on their role in a particular experiment, the genes that they are related to, or the various combinations that were used. For example agents of types "monoclonal antibody" can be related to the protein product to which it binds. Or agents of type "oligonucleotide" can be related to the mRNA gene product that they down regulate in anti-sense experiments. This also allows subsequent retrieval of experimental data based on the gene products which are either used as agents directly (e.g. transfection or direct addition of the gene product) or indirectly (e.g. The software system discussed in this disclosure can be implemented in a variety of database systems.

Figure 11:
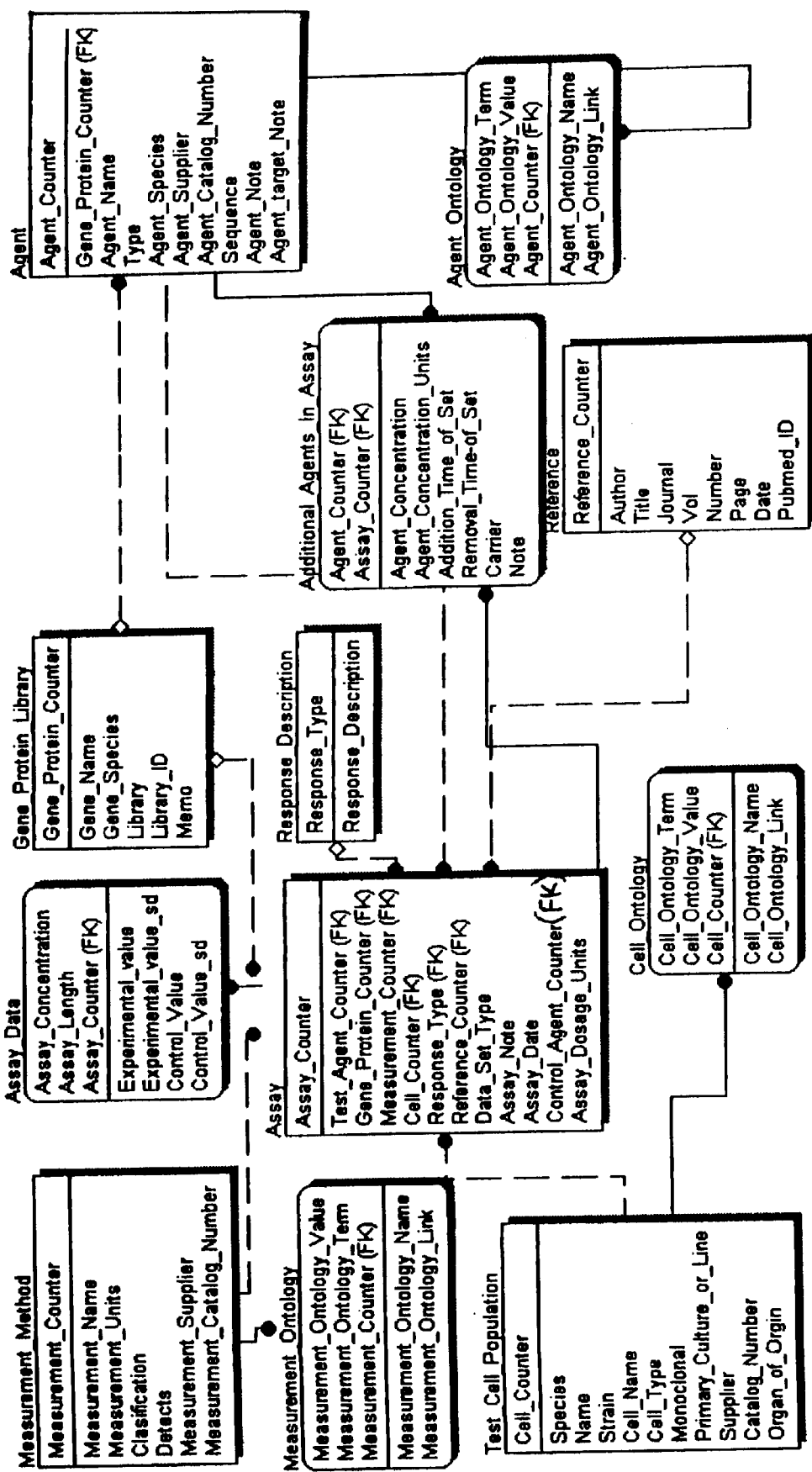
FIG. 11 illustrates the preferred relational links between fields in the above described libraries.

FIG. 11 illustrates the preferred relational links between fields in the above described libraries. The field-to-field assignments are shown by solid lines. First, the Agent, Method (used to measure the cellular response), Gene/Protein, Test Cell Population and Reference Library tables are presented. All these tables use an AutoNumber key field, and may be related to zero (or one) to many different assays in the Assay table. Also note the presence of the Gene/Protein key field as a foreign key in the Agent table. Next the tables for the entry of the general experimental design, and the specific experimental data are presented. These include the Assay table, the Additional Agents in Assay table, and the Assay Data Table. Note that the Assay table is linked to the five library tables by the presence of their AutoNumber Key Fields (or counter key fields) as foreign keys within the assay table. In the case of the Agent Table key field this actually occurs twice first for the Test Agent and Secondly for the Control Agent. Also, one Assay can have zero to many Additional Agents or one to many Assay Data Table entries. The entry of data can be further controlled by the use of indices that can for example. monitor duplicate entries.

Examples of suitable table structures for the above-described tables are given in FIGS. 12–21. The table structures are provided to give one operational example of field names and definitions for all of the above-described Agent (FIG. 12), Measurement Method (FIG. 13), Gene/Protein (FIG. 14), Test Cell Population (FIG. 15), Reference (FIG. 16), Assay (FIG. 17), Additional Agents (FIG. 18), and the Assay Data Table (FIG. 19). In addition, a table is included for Measurement_Ontology (FIG. 20). This table provides a means to allow measurements, cells and conditions to be coded by user-determined ontologies. The Agent, Method, and Test Cell Population tables are linked to similar tables to allow multiple codings with user defined ontologies. For example, the Unified Medical Language System (UMLS) has recently been made widely available by the National Library of Medicine. It is now possible to code methods such as tritiated thymidine incorporation, or DNA content by flow cytometry with the UMLS Concept Unique Identifier (CUI) for S-phase (C0080129). This allows subsequent searching for experiments measuring this biological property independent of the name of the specific method. Similarly, the CUIs for vascular smooth muscle (C0026844) and atherosclerosis (C004153) would code vascular smooth muscle cells isolated from an atherosclerotic lesion. The overall description of the experimental measurement is chosen from a list stored in the Response Description Table of FIG. 21.

Given the nature of data systems design, there are many equivalent embodiments of this system and minor differences in the field content of database tables are considered to be within the scope and spirit of this design. For example, a different method for specifying a data model may be used. For example, an Extensible Markup Language Document Type Definition or object oriented definitions for an equivalent database should be readily produced by one skilled in the art. Similarly, the Assay data Table can be modified to allow for array data in which the expression of numerous different protein or mRNA levels are measured at each point.

3. Data Querying

The above-described combination of data entry and storage allows the system to store important details of experimental design as well as the relationship between changes in the level of expression of target mRNAs/proteins and changes of cellular functional activity. The system supports flexible queries. Thus, queries such as "find all drugs related to a given protein product for which there is cellular function data" can now be supported. As biological research shifts from the reduction of biological pathways to understanding their interrelationships, this type of ability will become increasingly important.

For example FIG. 22 shows information for the test agent thalidomide (a Drug), while FIG. 23 shows all the additional agents thalidomide has been assayed with and the associated assay numbers.

FIG. 24 shows the relationships between a group of agents and their target genes, and FIG. 25 shows data from a query for cell lines coded for "vascular smooth muscle" (drugs, antibodies, anti-sense etc.).

In addition, the system supports the following features: 1) queries are not limited to a specific type of test cell population, or specific category of agents; 2) general cellular properties such as viability, adherence or proliferation may be queried; 3) the system allows the pattern of response (i.e. up or down regulation) of the assay to be queried; 4) information regarding the type of cell used (e.g. name, species and cell type) can be queried.

Other example queries are as follows:
1) Find all cell types tested against TGF β-1.
2) Find all patterns of response for TGF β-1 growth inhibition in the cell types noted above in.
3) For all cell types that lacked TGF β-1 induced growth inhibition, list all genes/proteins for which there is additional data.

No computer technical skills are required by any participants, except for the maintainers of the database. The queries are simple and preferably form-based. The forms can be made available via the Internet. It is envisioned that repositories can be maintained for specific areas of interest (by universities or other organizations) and journal editors in those areas of interest would manage the data input. By standardizing on the CRD data model, a researcher could design queries that would be valid regardless of the repository's site.

The present system is very efficient and effective for data reporting of a specific but important type of experimental design. The kinds of data warehouses that result will be of great use to researchers who need trend and summary information from a large group of experiments. As mentioned above, the present invention can be implemented in an XML (eXtensible Markup Language) model for electronic data interchange. The XML objects are plain text and are easily emailed or other wise transferred to the repository. Once at the repository, since they are highly structured objects, they can viewed with specialized viewers and/or exported to specialized databases such as the System described herein.

The above-described method provides the ability to store and query heterogeneous data using a single data model in order to minimize difficulties associated in searching multiple databases. It supports a broad range of data including protein or mRNA expressions, as well as functional cellular data such as apoptosis or adherence.

All of the foregoing forms and data libraries may be authored using conventional relational database software such as Microsoft Access®.

The above-described software method is combined with suitable hardware for implementation of the system for conversion, storage and querying of the data of cellular biological assays on the basis of experimental design. The system includes a conventional computer workstation, operating system, and the software-implemented process of the present invention. The computer workstation may be, for example, a conventional personal computer with standard internal components, e.g., a microprocessor with peripheral chipset mounted on an appropriate motherboard. Of course, other more or less powerful computer systems can be used, but it is suggested that the computer system meet the minimum system requirements for Microsoft Access '97 or an equivalent database operating system. The user interface is preferably a conventional color monitor, a modem, and a standard input device such as a mouse. The operating system is preferably Windows 95 or a later revision. All data entry forms may be maintained on the internet for user access, and a separate web server is required in this case.

The system software may be compressed onto a series of installation floppy diskettes, and may be loaded onto a computer system as described above using conventional installation macros such as provided with Windows 95.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the following claims.

We claim:

1. A method for supporting hypothesis driven queries of cellular biological assays on the basis of experimental design, comprising:
    collecting general assay method and materials information relating to test, control and additional agents, test cells, gene/proteins, and measurement methods through a first set of computer forms;
    incorporating said method and materials information into a second set of computerized forms and collecting general experimental design information based on said collecting step;

a third step of incorporating said method and materials information and general experimental design information into a third set of computerized forms and collecting specific experimental results data based on said collecting and incorporating steps;

maintaining a library of query forms for allowing a user to enter queries about the experimental effect of any agent, or combination of agents, on the test cell population.

2. The method for supporting hypothesis driven queries of cellular biological assays on the basis of experimental design according to claim 1, wherein said step of maintaining a library of query forms further comprises maintaining separate query forms for allowing a user to enter queries related to genes that said assays are related to, and for allowing a user to enter queries related to combinations of agents used in said assay.

* * * * *